United States Patent [19]

Garner et al.

[11] 4,007,195
[45] Feb. 8, 1977

[54] HETEROCYCLIC SUBSTITUTED FLUORANS

[75] Inventors: Robert Garner, Ramsbottom Bury, England; Jean Claude Petitpierre, Kaiseraugst, Switzerland

[73] Assignee: Ciba-Geigy AG, Basel, Switzerland

[22] Filed: Sept. 30, 1975

[21] Appl. No.: 618,102

Related U.S. Application Data

[62] Division of Ser. No. 507,158, Sept. 18, 1974, Pat. No. 3,929,831.

[52] U.S. Cl. .................. 260/293.58; 260/326.34; 260/326.5 CA; 260/326.85; 260/335; 260/247.5 H; 260/247.7 T; 260/293.56; 260/247.2 A; 260/295 T; 260/296 T; 260/297 T

[51] Int. Cl.² ........................................ C07D 271/00

[58] Field of Search ............... 260/326.34, 293.58, 260/335

[56] References Cited

UNITED STATES PATENTS 3,929,831   12/1975   Garner et al. ............... 260/326.34

*Primary Examiner*—Lewis Gotts
*Assistant Examiner*—Cary Owens
*Attorney, Agent, or Firm*—Joseph G. Kolodny; Edward McC. Roberts; Prabodh I. Almaula

[57] ABSTRACT

Heterocyclic substituted fluoran compounds of the formula

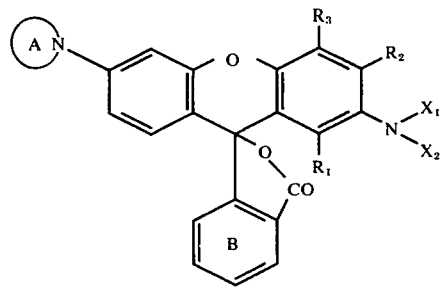

wherein
$R_1$, $R_2$ and $R_3$ independently of the other, represent hydrogen, alkyl with 1 to 4 carbon atoms, nitro or halogen or
$R_2$ and $R_3$ together complete a condensed carbocyclic ring,
$X_1$ and $X_2$ independently of the other, represent hydrogen, alkyl with 1 to 12 carbon atoms, alkenyl with at most 12 carbon atoms, alkoxyalkyl with 2 to 8 carbon atoms, alkoxycarbonylalkyl with 3 to 9 carbon atoms cycloalkyl with 5 or 6 carbon atoms, acyl having 1 to 12 carbon atoms, or optionally substituted benzyl, phenyl or naphthyl, and the nitrogen ring A represents a heterocyclic radical which optionally includes a further hetero atom as a ring member and the benzene ring B may be further substituted by nitro or 1 to 4 halogen atoms. These fluorans compounds are particularly useful as color formers which give intense dark green, grey black or red colors when they are brought into contact with an electron-accepting co-reactant.

6 Claims, No Drawings

HETEROCYCLIC SUBSTITUTED FLUORANS

This is a division of application Ser. No. 507,158 filed on Sept. 18, 1974, now U.S. Pat. No. 3,929,831, issued Dec. 30, 1975.

The present invention provides novel fluoran compounds which are normally colourless or only weakly coloured but which by variation of the substituents in position 2 can give intense dark green, grey-black or red colours when contacted with an electron accepting co-reactant. The invention specifically relates to fluoran compounds, having in position 6 a nitrogen heterocyclic residue attached to the fluoran system through the nitrogen atom, and in position 2 a substituted amino group; a process for the manufacture of such compounds and their use as colour formers in pressure-sensitive or thermo-reactive recording materials.

The new fluoran compounds according to the invention correspond to the formula

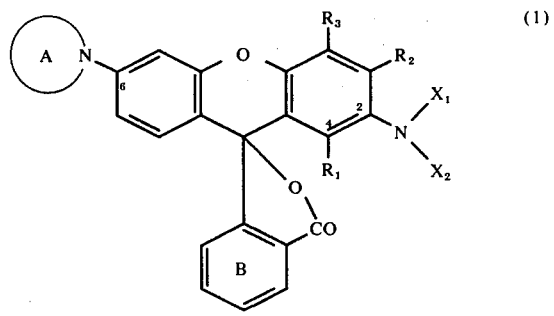

wherein $R_1$, $R_2$ and $R_3$ independently of the other, represent hydrogen, alkyl with 1 to 12 carbon atoms, nitro or halogen, or $R_2$ and $R_3$ together complete a condensed carbocyclic ring, especially a condensed benzene or tetrahydro benzene ring, $X_1$ and $X_2$ independently of the other, represent hydrogen, alkyl with 1 to 12 carbon atoms, alkenyl with at most 12 carbon atoms, alkoxyalkyl with 2 to 8 carbon atoms, alkoxycarbonylalkyl with 3 to 9 carbon atoms, cycloalkyl with 5 or 6 carbon atoms, acyl having 1 to 12 carbon atoms, or optionally substituted phenyl, naphthyl or benzyl, the nitrogen ring A represents a heterocyclic radical which optionally includes a further hetero atom as ring member, especially oxygen, sulphur or nitrogen, and the benzene ring B may be substituted by nitro or 1 to 4 halogen atoms.

Halogen, in each occurrence in the definitions of the substituents, preferably stands for fluorine, bromine or especially chlorine.

When $R_1$, $R_2$ and $R_3$, as well as $X_1$ and $X_2$ represent alkyl, they may be straight or branched chain alkyl groups. Examples of said alkyl groups are methyl, ethyl, n-propyl, iso-propyl, n-butyl, sec.butyl or tert.butyl, octyl or dodecyl. $R_1$, $R_2$ and $R_3$ are preferably hydrogen, halogen or alkyl having 1 to 4 carbon atoms such as methyl or ethyl.

Alkenyl in $X_1$ and $X_2$ stands e.g. for allyl, 2-methallyl, 2-ethylallyl, 2-butenyl or octenyl.

Alkoxyalkyl and Alkoxycarbonylalkyl in $X_1$ and $X_2$ may have 1 to 4 carbon atoms in each alkyl part and stand preferably for β-methoxyethyl or β-ethoxyethyl and β-methoxycarbonylethyl or β-ethoxycarbonylethyl, respectively.

Cycloalkyl in the meaning of these X-radicals may be cyclopentyl or preferably cyclohexyl. The optional substituents in the benzyl, phenyl or naphthyl group may be alkyl with 1 to 4 carbon atoms, alkoxy with 1 to 4 carbon atoms, alkoxycarbonyl with 2 to 5 carbon atoms, acyl having 1 to 4 carbon atoms, nitro, halogen or an amino group optionally substituted by alkyl with 1 to 4 carbon atoms or by benzyl. Examples of these aromatic or araliphatic radicals are p-methylbenzyl, p-chlorobenzyl, p-nitrobenzyl, p-tolyl, xylyl, p-chlorphenyl, p-nitrophenyl, 1-methylnaphthyl-(2) or 2-methylnaphthyl-(1).

Among the acyl groups the alkanoyl groups containing 1 to 12 carbon atoms, such as formyl, acetyl or propionyl are especially noteworthy. Further acyl substituents may be alkylsulphonyl having 1 to 12 carbon atoms, such as methylsulphonyl, as well as benzoyl or benzenesulphonyl groups which may be substituted in benzene ring by halogen, methyl or methoxy groups.

In the fluoran compounds falling under formula (1), the nitrogen ring A denotes a heterocyclic radical which is attached to the fluoran ring through the nitrogen atom. The heterocyclic radical may have 3 to 12, preferably 5 or 6 ring members, wherein 1 or 2 hetero atoms may be included as ring members. It is for instance a pyrrolidinyl, piperidino, pipecolino, perhydroazepinyl, heptamethyleneimino, octamethylenimino, 1,2,3,4-tetrahydroquinolinyl, indolinyl or hexahydrocarbazolyl group, or in case the hetero ring includes a further hetero atom, a morpholino, thiomorpholino, piperazino, N-alkyl piperazino with 1 to 4 carbon atoms in the alkyl part, or a pyrazolinyl or 3-methylpyrazolinyl group.

As halogen, the benzene ring B may contain fluorine, bromine or especially chlorine. Preferably, it is not further substituted or contains 4 chlorine atoms.

Practically important groups of the compounds of formula (1) may be defined by the following formula

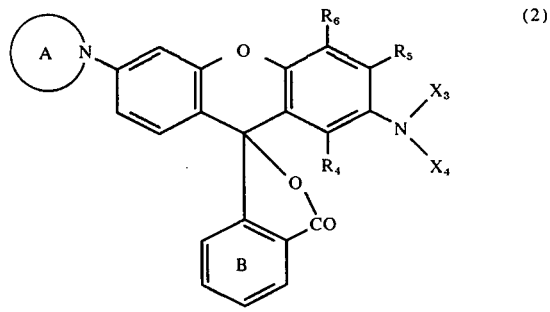

wherein $R_4$, $R_5$ and $R_6$ independently of the other, represent hydrogen, halogen, methyl or ethyl, $X_3$ represents alkyl with 1 to 8 carbon atoms, alkoxyalkyl with 2 to 8 carbon atoms, cycloalkyl with 5 or 6 carbon atoms, acyl with 1 to 7 carbon atoms, phenyl or benzyl optionally substituted in the ring by methyl or halogen, $X_4$ represents hydrogen, alkyl with 1 to 8 carbon atoms, cycloalkyl with 5 or 6 carbon atoms, acyl with 1 to 7 carbon atoms or benzyl optionally substituted in the ring by methyl or halogen, and the nitrogen ring A and the benzene ring B have the given meanings.

Particularly useful fluoran compounds of the formulae (1) and (2) may be represented by the formula

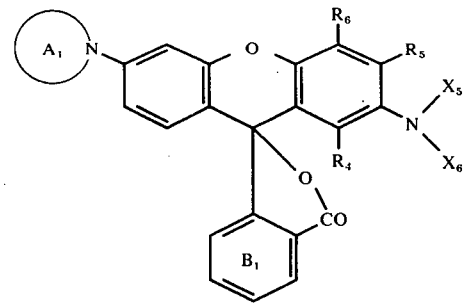

(3)

wherein $R_4$, $R_5$ and $R_6$ have the meaning given under formula (2), $X_5$ represents alkyl with 1 to 8 carbon atoms, acyl with 1 to 7 carbon atoms, phenyl or benzyl, $X_6$ represents hydrogen, alkyl with 1 to 8 carbon atoms, acyl with 1 to 7 carbon atoms or benzyl, the nitrogen ring $A_1$ represents a morpholino, piperazino or especially a pyrrolidinyl or piperidino ring and the benzene ring $B_1$ may be further substituted by 1 to 4 halogen atoms, especially chlorine atoms.

Of special interest are fluoran compounds falling under formulae (1) to (3), which are listed under A, B and C, respectively.

A. Compounds of the formula

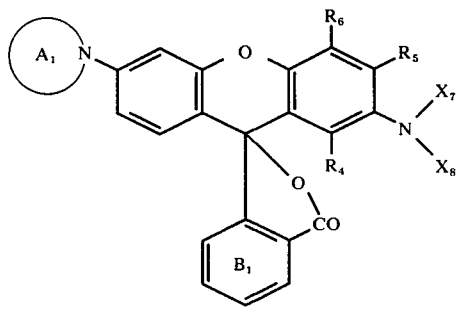

(4)

wherein $A_1$, $B_1$, $R_4$, $R_5$ and $R_6$ have the meaning given under formula (3), $X_7$ and $X_8$ independently of the other, represent alkyl with 1 to 8 carbon atoms or benzyl.

These fluoran compounds are distinguished as dark green colour formers.

B. Compounds of the formula

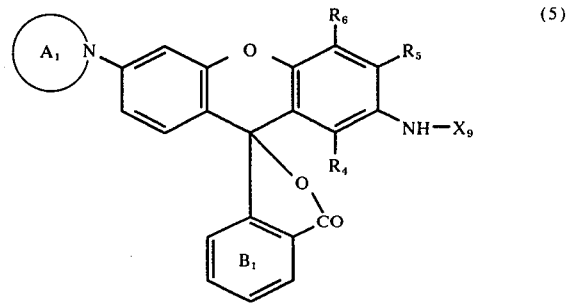

(5)

wherein $A_1$, $B_1$, $R_4$, $R_5$ and $R_6$ have the meaning given under formula (3) and $X_9$ represents alkyl with 1 to 8 carbon atoms, benzyl or phenyl.

These fluoran compounds are colour formers which give a grey or black colour when contacted with an electron accepting co-reactant.

C. Compounds of the formula

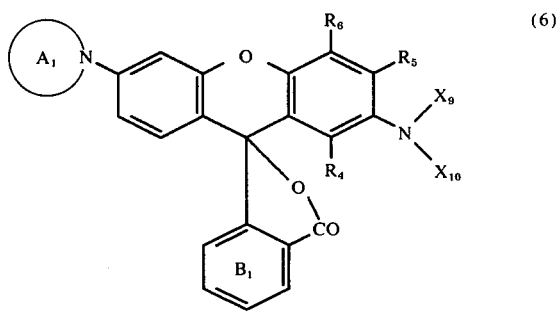

(6)

wherein $A_1$, $B_1$, $R_4$, $R_5$, $R_6$ and $X_9$ have the given meanings and $X_{10}$ represents acyl having 1 to 7 carbon atoms, for example, alkanoyl with 1 to 4 carbon atoms, such as formyl, acetyl or propionyl, or benzoyl, methylsulphonyl or p-tolylsulphonyl.

These fluoran compounds are scarlet-red colour formers.

The new fluoran compounds of the formulae (1) to (6) are obtained by a method known in the art. The process of manufacturing the fluoran compounds of formula (1) comprises reacting a benzophenone compound of the formula

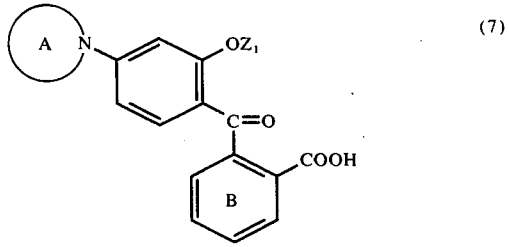

(7)

with a compound of the formula

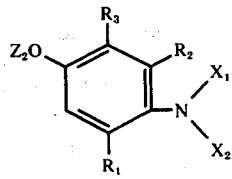

(8)

wherein A, B, $R_1$, $R_2$, $R_3$, $X_1$ and $X_2$ have the given meanings and $Z_1$ and $Z_2$ represent hydrogen or alkyl having 1 to 4 carbon atoms, such as methyl, ethyl or butyl. Preferably, of $Z_1$ and $Z_2$ one is hydrogen, methyl or ethyl and the other is hydrogen. Most preferably, $Z_1$ is hydrogen and $Z_2$ is hydrogen or methyl.

The reaction is advantageously carried out at 10° to 100° C by allowing the reactants of formulae (7) and (8) to react together in the presence of an acidic condensing agent.

Examples of suitable condensing agents are acetic anhydride, sulphuric acid, zinc chloride or phosphorous oxychloride. This reaction is preferably completed by the addition of a base. The bases may be organic or inorganic and can include, for example, alkali metal hydroxides, such as sodium hydroxide or potassium hydroxide, as well as aliphatic amines, such as triethylamine or trihydroxyethylamine.

The starting compounds of formula (7) are new and are generally prepared by reacting a phthalic anhydride of the formula

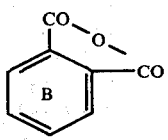

(9)

with a compound of the formula

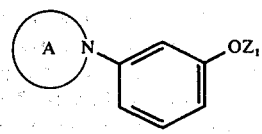

(10)

wherein $Z_1$ represents hydrogen or alkyl having 1 to 4 carbon atoms and A and B have the meaning described above. This reaction is suitably carried out in an organic solvent, such as acetone, benzene, toluene, xylene, or a chlorobenzene, preferably at temperatures at or below the boiling point of such solvents.

The compounds of formula (10) may be produced by condensing the heterocyclic base (A)NH, in which the cycle A has the meaning described above, with resorcinol or a monoalkyl ether derivative thereof at temperatures between 50° and 250° C and optionally under pressure. This reaction may or may not be assisted by the use of a condensing agent, examples of which are zinc chloride, aluminium chloride or sulphanilic acid. Alternatively, the compounds of formula (10) may be prepared from the reaction of meta hydroxy- or alkoxyaniline with a $\alpha,\omega$-dihalogenoalkanes in which the halogen is, for example, bromine or chlorine but more usually bromine.

Compounds of formula (1), wherein $X_1$ or $X_2$ or both represent acyl may be manufactured by reacting a compound of formula (1), wherein at least one of $X_1$ and $X_2$ represents hydrogen, with acylating agents having at most 12 carbon atoms, e.g. reactive functional derivatives of aliphatic carboxylic or sulphonic acids, particularly fatty acid halides and anhydrides such as acetyl chloride, acetyl bromide or acetic anhydride or of aromatic carboxylic or sulphonic acids such as benzoic acid halides or benzene sulphonic acid halides.

The acylation is generally carried out by known methods, e.g. in the presence of acid binding agents such as alkali metal carbonates or tertiary nitrogen bases such as pyridine and optionally in the presence of inert organic solvents such as acetone, isopropanol, chlorobenzene or nitrobenzene.

The new fluorans, according to the invention, are more or less colourless compounds which are particularly useful when they are brought into contact with an acidic co-reactant substance, that is an electron-accepting substance. Typical co-reactants are, for example, attapulgus clay, silton clay, silica, bentonite, halloysite, aluminium oxide, aluminium phosphate, kaolin or any acidic clay, or an acid reacting polymeric material such as a phenolic polymer, an alkylphenol acetylene polymer, a maleic acid-rosin resin or a partially or wholly hydrolysed polymer of maleic anhydride with styrene, ethylene, vinyl methylether or carboxy polymethylenes.

The prefereed co-reactants are attapulgus clay, silton clay or a phenol-formaldehyde resin, these electron acceptors, preferably, are coated on the front side of the receiving sheet.

As indicated above, the fluoran compounds of formula (4) behave as dark green colour formers, while compounds of formula (5) behave as grey or black colour formers. On the other side, the fluoran compounds of the formula (6) behave as red or scarlet-red colour formers.

By varying the structure of this new range of fluorans certain properties may be "built-in," for example, the colour as described in the previous paragraph, fade stability for compatibility with other colour formers in mixtures, and any solubility characteristics which would allow greater flexibility in the choice of solvents used in microencapsulation and other modes of application.

As already mentioned, these colour formers above all are suitable for the use in so-called pressure-sensitive recording material. Such a material e.g. includes at least one pair of sheets, which comprises at least a colour former of formula (1) dissolved in an organic solvent, preferably contained in pressure rupturable microcapsules and an electron accepting substance.

The colour former, upon coming into contact with the electron accepting substance being able to produce a coloured marking at the points where the pressure is applied.

These colour formers which are comprised in the pressure-sensitive copying material are prevented from becoming active by being separated from the electron accepting substance. As a rule this is done by incorporating these colour formers into a foam-, sponge- or honeycomb-like structure. Preferably however these colour formers are microencapsulated.

When these colourless colour formers of formula (1) are dissolved in an organic solvent, they may be subjected to a microencapsulation process and subsequently used for making pressure-sensitive papers. When the capsules are ruptured by pressure from e.g. a pencil and the colour former solution is thus transferred into an adjacent sheet coated with a substrate capable of acting as an electron acceptor, a coloured image is produced. This new colour results from the thus produced dyestuff which absorbs in the visible region of the electromagnetic spectrum.

The general art of making microcapsules of some character has long been known. Well known methods e.g. are disclosed in U.S. Pat. Nos. 2,183,053, 2,800,457, 2,800,458, 3,265,630, 2,964,331, 3,418,656, 3,418,250, 3,016,308, 3,424,827, 3,427,250, 3,405,071, 3,171,878, and 2,797,201. Further methods are disclosed in British Patent Specifications 989,264 and above all 1,156,725. Any of these and other methods are suitable for encapsulating the present colour formers.

Preferably the present colour formers are encapsulated dissolved in organic solvents. Suitable solvents are preferably non-volatile e.g. polyhalogenated diphenyl such as trichlorodiphenyl and its mixture with liquid paraffin, tricresyl phosphate, di-n-butyl phthalate, dioctyl phthalate, trichlorobenzene nitrobenzene, trichloroethyl-phosphate, petroleumether, hydrocarbon oils, such as paraffin, condensated derivatives of diphenyl or triphenyl, chlorinated or hydrogenated condensed aromatic hydrocarbons. The capsule walls preferably have been obtained by coacervation forces evenly around the droplets of the colour former solution, the encapsulating material consisting of gelatine, as e.g. described in U.S. Pat. No. 2,800,457.

Alternatively, the capsules preferably may be made of aminoplast or modified aminoplasts by polycondensation as described in British Patent Specification 989,264 or 1,156,725.

A preferred arrangement is wherein the encapsulated colour former is coated on the back side of a transfer sheet and the electron accepting substance is coated on the front side of a receiving sheet.

In another preferred material one or more of the new fluorans are co-encapsulated with one or more other known colour formers, such as crystal violet lactone, benzoyl leuco methylene blue, or a bis-indolyl phthalide such as 3,3-bis(1'-n-octyl-2'-methylindol-3'-yl)-phthalide.

The microcapsules containing the colour formers of formula (1) are used for making pressure-sensitive copying material of the various types known in the art, such as so called "Chemical Transfer" and "Chemical Self-contained" papers. The various systems mainly are distinguished by the arrangement of the capsules, the colour reactants and the support material.

The microcapsules may be in an undercoating of the upper sheet and the colour reactants, that is the electron acceptor and coupler, may be in the overcoating of the lower sheets. However, the components may also be used in the paper pulp. Such systems are called Chemical Transfer system.

Another arrangement we have in the self-contained papers. There the microcapsules containing the colour former and and the colour reactants are in or on the same sheet as one or more individual coatings or in the paper pulp.

Such pressure-sensitive copying materials are described e.g. in U.S. Pat. Nos. 3,516,846, 2,730,457, 2,932,582, 3,427,180, 3,418,250 and 3,418,656. Further systems are disclosed in British Patent Specifications 1,042,597, 1,042,598, 1,042,596, 1,042,599, 1,053,935 and 1,517,650. Microcapsules containing the colour formers of formula (1) are suitable for any of these and other systems.

The capsules are preferably fixed to the carrier by means of a suitable adhesive. Since paper is the preferred carried material, these adhesives are predominantly paper coating agents, such as e.g. gum arabic, polyvinyl alcohol, hydroxymethylcellulose, casein, methylcellulose or dextrin.

In the present application, the definition "paper" not only includes normal papers from cellulose fibres, but also papers in which the cellulose fibres are replaced (partially or completely) by synthetic fibres of polymers.

The new fluoran compounds may also be used as colour former in thermoreactive recording material comprising at least a support, a binder, a colour former and an electron accepting substance. Thermoreactive recording systems comprise heat-sensitive recording and copying materials and papers. These systems are used e.g. for the recording of information, for example, in electronic computers, in teleprinters or telewriters, in measuring instruments. The mark-forming also can be made manually with a heated pen. A further means for inducing heat-initiated marks are laser beams. The thermoreactive recording material may be arranged in such a manner that the colour former is dissolved or dispersed in a layer of the binder, and in a second layer the developer and the electron-accepting substance are dissolved or dispersed in the binder. Another possibility consists in dispersing both the colour former and the developer in one layer. By means of heat the binder is softened at specific areas imagewise and the dyestuff is formed at these points, since only at the points where heat is applied does the colour former come into contact with the electron-accepting substance.

The developers are the same electron-accepting substances as are used in pressure sensitive papers. For practical reasons the developer should be solid at room temperature and melt or evaporate above 50° C. Examples of such products are the already mentioned clays, phenolic resins, phenolic compounds such as 4-tert.-butylphenol, 4-phenylphenol, 4-hydroxydiphenyloxide, α-naphthol, 4-hydroxybenzoic acid methyl ester, β-naphthol, 4-hydroxyacetophenone,2,2'-dihydroxydiphenyl, 4,4'-isopropylidene-diphenol, 4,4'-isopropyliden-bis-(2-methylphenol), 4,4'-bis-(hydroxyphenyl) valeric acid, hydroquinone, pyrogallol, phloroglucinol, p-, m-, o-hydroxybenzoic acid, gallic acid, 1-hydroxy-2-naphthoic acid, boric acid, and the aliphatic dicarboxylic acids e.g. tartaric acid, oxalic acid, maleic acid, citraconic acid or succinic acid.

Preferably fusible, film-forming binders are used. These binders should be water-soluble, since the nitrophthalides and the developer are water-insoluble. The binder should be able to disperse and fix the colour former and the developer at room temperature. In this way the two reactive components are present in the material in a non-associated form. After applying heat, the binder softens or melts, which enables the colour former to come into contact with the developer and to form a dyestuff.

Water-soluble or at least water swellable binders are e.g. hydrophilic polymers such as polyvinyl alcohol, polyacrylic acid, hydroxyethylcellulose, methylcellulose, carboxymethylcellulose, polyacrylamide, polyvinylpyrrolidone gelatine or starch.

In so far as the colour former and the developer are coated in two separate layers, binders which are water-insoluble may be used, i.e. binders soluble in non-polar or only weakly polar solvents, e.g. natural rubber, synthetic rubber, chlorinated rubber, alkyd resins, polystyrene, styrene-butadienecopolymers, polymethylmethacrylates, ethylcellulose, nitrocellulose or polyvinylcarbazole.

The preferred arrangement, however, is colour former and developer in a water-soluble binder in one layer.

The coatings of the thermoreactive material may contain further additives. To improve the degree of whiteness, to ease the printing of the papers and to prevent the sticking of the heated pen, these materials may contain e.g. talc, $TiO_2$, ZnO or $CaCO_3$. In order to produce the dyestuff only within a limited temperature range there may be added substances such as urea, thiourea, acetanilide, phthalic acid anhydride or other corresponding meltable products which induce the simultaneous melting of colour former and developer.

Typical thermoreactive recording materials wherein the present colour formers may be used e.g. are described in German Patent Application 2,228,581, French Patent 1,524,826, Swiss Patent 407,185, German Patent Application 2,110,854, Swiss Patents 164,976, 444,196 and 444,197.

The following non-limitative examples illustrate the present invention. Percentages are expressed by weight, unless otherwise stated.

EXAMPLE 1

2-(N,N-dibenzylamino)-6-N-pyrrolidinylfluoran

A mixture of 77.75 g 2'-carboxy-2-hydroxy-4-N-pyrrolidinylbenzophenone, 75.6 g N,N-dibenzyl-p-anisidine and 250 ml 98% sulphuric acid is stirred at 60° C for 5 hours and then quenched into 2750 ml ice water to precipitate a solid. The solid is filtered off, washed with water and added to a mixture of 500 ml water, 250 ml methanol and 26.8 g sodium hydroxide at 70° C. The mixture is boiled for 2 hours and then cooled to 85° C. The solid product is filtered off, washed with hot water then recrystallized from methanol/acetone and dried to yield 86 g white plates m.p. 180° C. λ max. in 95% acetic acid 435, 462 and 607 nm.

A solution of the 2-(N,N-dibenzylamino)-6-N-pyrrolidinyl-fluoran in a hydrogenated terphenyl solvent gives a dark green print when applied to silton clay coated paper. Absorption maxima are observed at λ 444 and 602 nm.

The benzophenone compound used in this example as starting material may be produced as follows. A mixture of 74 g phthalic anhydride, 81.5 g 1-(3'-hydroxyphenyl)pyrrolidine and 335 ml xylene is heated at 125° C. for 6 hours, then cooled to 25° C. The precipitate is filtered off, washed with methanol and dried to yield 110.5 g yellow solid having m.p. 194° C after crystallisation from ethanol.

EXAMPLE 2

2-Ethylamino-6-N-pyrrolidinylfluoran fluoran

A mixture of 9.33 g 2'-carboxy-2-hydroxy-4-N-pyrrolidinylbenzophenone, 4.54 g N-ethyl-p-anisidine and 30 ml 98% sulphuric acid is stirred at 60° C for 5 hours and then quenched into 330 ml ice-water to precipitate a solid. The solid is filtered off, washed with water and added to 75 ml methanol and 16.5 ml triethylamine. The mixture is boiled with stirring for 12 hours, then cooled to 0° C. The precipitate is filtered off, washed with methanol and dried to yield 8,32 g of 2-ethylamino-6-N-pyrrolidinylfluoran as a white solid. λ max. in 95% acetic acid 434, 457 and 602 nm.

A solution of this compound in benzene is colourless and gives a black colour on contact with silica, greenish black on attapulgus or silton clay and green on phenolic resin.

EXAMPLE 3

2-N-Acetyl-N-ethylamino-6-N-pyrrolidinyl fluoran

A mixture of 4,0 g 2-ethylamino-6-N-pyrrolidinyl fluoran, 12 ml acetic anhydride and 0,4 ml pyridine is stirred at 120° C for 4 hours. The solution is then evaporated to dryness, the residue taken up in 20 ml 10% sodium carbonate solution and extracted with ether. After drying and evaporating of the ether, 3,2 g of 2-N-acetyl-N-ethylamino-6-N-pyrrolidinyl fluoran are obtained. λ max. in 95% acetic acid 374,496 and 528 nm.

This compound forms a red colour when brought in contact with electron accepting substances such as silica.

EXAMPLE 4

2-(N,N-dibenzylamino)-6-N-pyrrolidinylfluoran

A mixture of 15,5 g 2'-carboxy-2-ethoxy-4-N-pyrrolidinylbenzophenone and 14,45 g p-dibenzylaminophenol is stirred in 50 ml 98% sulphuric acid at 60° C for 5 hours, cooled to 25° C and drowned into a mixture of 100 ml water and 450 g ice. The pH of the quenched mass is adjusted to 8.5 with 120 ml 35% to ammonia solution. The precipitate is filtered off, washed with water and dried at 70° C in vacuo to yield 19,7 g of 2-dibenzylamino-6-N-pyrrolidinylfluoran. The product is recrystallized from a mixture of methanol and acetone to yield colourless plates having a melting point of 180° C. This product is identical with the colour former obtained according to Example 1.

The 2'-carboxy-2-ethoxy-4-N-pyrrolidinyl-benzophenone compound used in this example as starting material may be produced as follows. To a mixture of 31.1 g 2'-carboxy-4-N-pyrrolidinyl-2-hydroxybenzophenone, 39.6 ml diethyl sulphate and 240 ml acetone at 35° C, is added a solution of 16.8 g potassium hydroxide in 50 ml water, drop-wise over 4 hours. The reaction mxiture is then stirred for a further 20 hours at 35°–40° C. A solution of 11.2 g potassium hydroxide in 50 ml water is then added and the reaction mixture is heated to boiling and refluxed for 2 hours. The solvent is distilled off until the temperature of the residual solution is 96° C. The residue is held at 96° C for 30 minutes then cooled down to 0° C by the addition of ice. Approximately 25 ml 28% HCl is added to bring the pH between 3 – 4 when the product precipitates as a white suspension. After filtering off and washing with water 32.0 g 2'-carboxy-4-N-pyrrolidinyl-2-ethoxybenzophenone, melting point 184°–5° C, is obtained.

EXAMPLE 5

2-Anilino-3-methyl-6-N-pyrrolidinyl fluoran 15 g 2'-carboxy-2-hydroxy-4-N-pyrrolidinylbenzophenone and 9,9 g 4-anilino-m-cresol are dissolved in 50 ml of 96° C sulphuric acid and stirred for 2 hours at 60° C. The product is washed up in a manner analogous to Example 2 and recrystallised from ethyl acetate/hexane, m.p. > 260° C. λ max. in 95% acetic acid 380,450 and 585 nm. When applied to paper coated with silton clay as described in Example 1 a grey print is obtained which gives absorption maxima at λ 453 and 575 nm.

By using procedures similar to those described in Examples 1 to 5 the fluoran compounds of the formula (11) listed in the following Table have been manufactured.

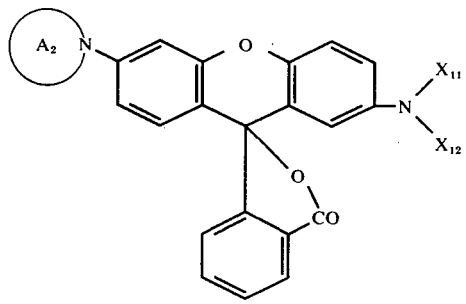

with silton clay, attapulgite clay or phenolic resin a dark green image is obtained after application of pressure by writing. Similar effect can be obtained by using any other colour former of the Examples 2 to 24.

EXAMPLE 26

Preparation of Pressure-sensitive Copying Paper

A solution containing 1.6 g of 2-dibenzylamino-6-N-pyrrolidinylfluoran, 0.6 g of 3,3-bis(1'-n-octyl-2'-methylindol-3'-yl)phthalide, 0.1 g of Crystal violet lactone and 0.6 g of benzoyl leuco methylene blue in 100 g of hydrogenated terphenyl is emulsified at 50° C in 100 g of 12% pigskin gelatin solution. 100 g of 12% gum arabic solution is added followed by 200 ml of water at 50° C. The emulsion is poured into 600 g ice-water and stirred for three hours to complete the coacervation. The resulting capsule slurry is coated into paper and dried. When the coated side is placed in contact with a second sheet coated with silton clay or attapulgite clay a grey-black image is obtained after application of pressure by writing.

| Ex. No. | $A_2$ | $X_{11}$ | $X_{12}$ | m.p. °C | λ maxima in nm 95% acetic acid | | | Silton clay | |
|---|---|---|---|---|---|---|---|---|---|
| 6 | N-Pyrrolidinyl | H | n-$C_4H_9$ | 202–203 | 435 | 459 | 599 | 446 | 582 |
| 7 | " | H | n-$C_8H_{17}$ | 172–173 | 435 | 459 | 600 | 450 | 588 |
| 8 | " | H | n-$C_{10}H_{21}$ | 128–130 | 433 | 457 | 600 | 450 | 582 |
| 9 | " | H | —⟨C₆H₅⟩ | 221–223 | | 447 | 600 | — | |
| 10 | " | $CH_3$ | $CH_3$ | 247–248 | 439 | 467 | 605 | 460 | 580 |
| 11 | " | $C_2H_5$ | $C_2H_5$ | 210–211 | 444 | 472 | 633 | 474 | 636 |
| 12 | " | n-$C_6H_{13}$ | n-$C_6H_{13}$ | 65–66 | 444 | 474 | 640 | 472 | 642 |
| 13 | " | —$CH_2$—⟨C₆H₅⟩ | n-$C_8H_{17}$ | 88–90 | 441 | 469 | 623 | 452 | 624 |
| 14 | " | —$CH_2$—⟨C₆H₅⟩ | n-$C_{12}H_{25}$ | oil | 440 | 470 | 622 | — | |
| 15 | " | —$CH_2$—⟨C₆H₅⟩ | —⟨C₆H₅⟩ | 112–115 | 440 | 460 | 605 | 452 | 602 |
| 16 | " | —$CH_2$—⟨C₆H₄⟩—Cl | —$CH_2$—⟨C₆H₄⟩—Cl | 128–130 | 435 | 463 | 608 | — | |
| 17 | " | —⟨C₆H₅⟩ | $CH_3$ | 206–208 | 444 | 456 | 605 | 458 | 576 |
| 18 | " | —CHO | n-$C_4H_9$ | 158–160 | | 501 | 532 | 504 | |
| 19 | " | —CHO | n-$C_8H_{17}$ | 120–121 | | 501 | 532 | 504 | |
| 20 | " | —$COCH_3$ | n-$C_4H_9$ | 112–115 | | 498 | 529 | 500 | |
| 21 | " | —$COCH_3$ | n-$C_8H_{17}$ | 77–79 | | 498 | 529 | 500 | |
| 22 | " | —CO—⟨C₆H₅⟩ | n-$C_4H_9$ | 177–178 | | 501 | 535 | 500 | |
| 23 | " | —CO—⟨C₆H₅⟩ | n-$C_8H_{17}$ | 199–200 | | 503 | 535 | 504 | |
| 24 | N-Piperidino | H | n-$C_8H_{17}$ | 143–144 | 439 | 467 | 605 | 450 | 584 |

APPLICATION EXAMPLES

EXAMPLE 25

Preparation of Pressure-sensitive Copying Paper

A solution containing 3 g of 2-dibenzylamino-6-N-pyrrolidinylfluoran in 100 g of hydrogenated terphenyl is emulsified at 50° C in 100 g of 12% pigskin gelatin solution. 100 g of 12% gum arabic solution is added followed by 200 ml of water at 50° C. The emulsion is poured into 600 g ice-water and stirred for three hours to complete the coacervation. The resulting capsule slurry is coated onto paper and dried. When the coated side is placed in contact with a second sheet coated

EXAMPLE 27

Preparation of Thermoreactive Paper 6 g of an aqueous dispersion containing 1.6% of 2-dibenzylamino-6-N-pyrrolidinylfluoran, 0.8% of 3,3-bis(1'-n-octyl-2'-methylindol-3'-yl)phthalide, 0.1% of Crystale violet lactone and 6.7% polyvinyl alcohol are mixted with 134 g of an aqueous dispersion containing 14% 4,4'-isopropylidenediphenol and 6% polyvinylacohol, the mixture is then coated on paper and dried. When contacted with a heated stylus a grey-black mark is obtained which has excellent light fastness.

EXAMPLE 28

Preparation of Thermoreactive Paper

When the colour formers in Example 27 are replaced by 2-dibenzylamino-6-N-pyrrolidinylfluoran and 3,3-bis(1'-n-octyl-2'-methylindol-3'-yl)phthalide in the ratio 6:4 the resulting system gives an intense black image.

We claim:

1. A fluoran compound of the formula

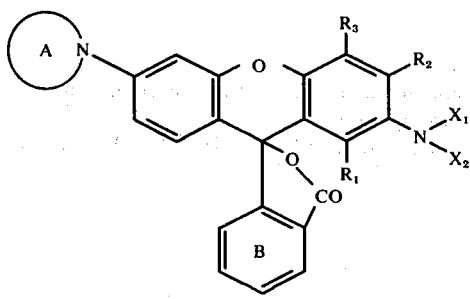

wherein $R_1$, $R_2$ and $R_3$ independently of the other, represent hydrogen, alkyl with 1 to 4 carbon atoms, nitro or halogen, or $R_2$ and $R_3$ together complete a condensed carbocyclic ring, $X_1$ and $X_2$ independently of the other, represent hydrogen, alkyl with 1 to 12 carbon atoms, alkenyl with at most 12 carbon atoms, alkoxyalkyl with 2 to 8 carbon atoms, alkoxycarbonylalkyl with 3 to 9 carbon atoms, cycloalkyl with 5 or 6 carbon atoms, acyl having 1 to 12 carbon atoms, or an unsubstituted or substituted benzyl, phenyl or naphthyl radical substituted by substituents selected from the group consisting of alkyl with 1 to 4 carbon atoms, alkoxy with 1 to 4 carbon atoms, alkoxycarbonyl with 2 to 5 carbon atoms, acyl having 1 to 4 carbon atoms, nitro, halogen or an amino optionally substituted by alkyl with 1 to 4 carbon atoms or by benzyl, and the nitrogen ring A represents the piperidino radical and the benzene ring B is unsubstituted or substituted by nitro or 1 to 4 halogen atoms.

2. A fluoran compound according to claim 1, of the formula

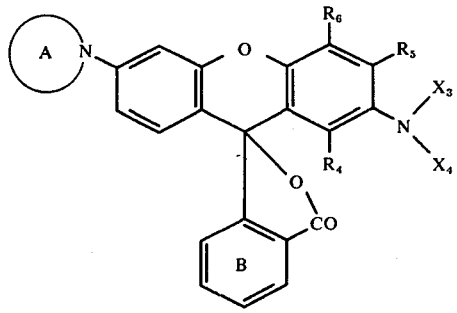

wherein $R_4$, $R_5$ and $R_6$ independently of the other represent hydrogen, halogen, methyl or ethyl, $X_3$ represents alkyl with 1 to 12 carbon atoms, alkoxyalkyl with 2 to 8 carbon atoms, cycloalkyl with 5 or 6 carbon atoms, acyl with 1 to 7 carbon atoms, phenyl or benzyl which is unsubstituted or substituted in the ring by methyl or halogen, $X_4$ represents hydrogen, alkyl with 1 to 8 carbon atoms, cycloalkyl with 5 or 6 carbon atoms, acyl with 1 to 7 carbon atoms, or benzyl unsubstituted or substituted in the ring by methyl or halogen.

3. A fluoran compound according to claim 2, of the formula

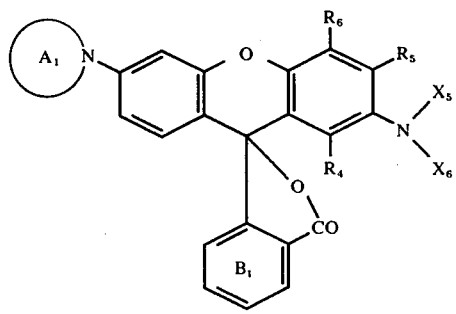

wherein $X_5$ represents alkyl with 1 to 12 carbon atoms, acyl with 1 to 7 carbon atoms, phenyl, benzyl or chlorobenzyl, $X_6$ represents hydrogen, alkyl with 1 to 8 carbon atoms, acyl with 1 to 7 carbon atoms, benzyl or chlorobenzyl, and the nitrogen ring $A_1$ represents piperidino and the benzene ring $B_1$ is unsubstituted or substituted by 1 to 4 halogen atoms.

4. A fluoran compound according to claim 3, of the formula

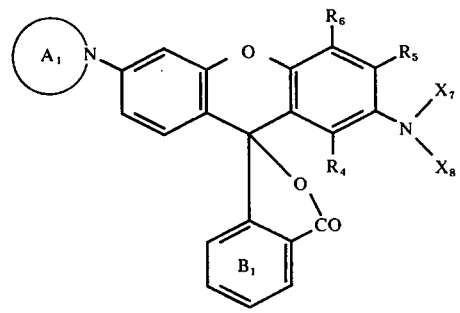

wherein $X_7$ and $X_8$ represent, independently of the other, alkyl with 1 to 8 carbon atoms, benzyl or chlorobenzyl.

5. A fluoran compound according to claim 3, of the formula

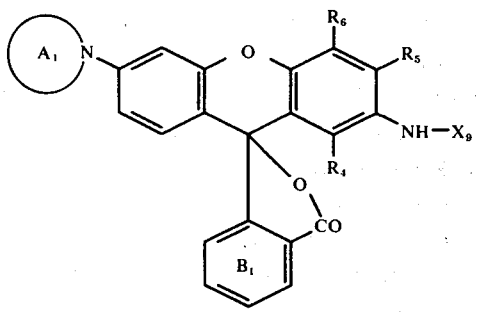
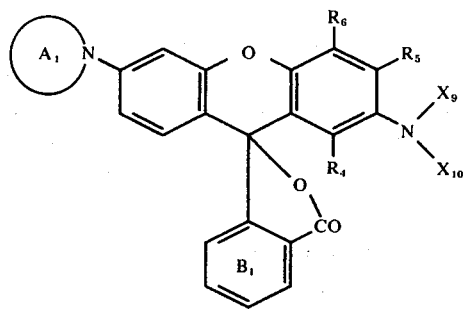
wherein
X₉ represents alkyl with 1 to 12 carbon atoms, benzyl or phenyl.
6. A fluoran compound according to claim 3, of the formula
wherein
X₉ represents alkyl with 1 to 8 carbon atoms, benzyl or phenyl and
X₁₀ represents acyl having 1 to 7 carbon atoms.
* * * * *

Notice of Adverse Decision in Interference

In Interference No. 101,590, involving Patent No. 4,007,195, R. Garner and J. C. Petitpierre, HETEROCYCLIC SUBSTITUTED FLUORANS, final judgment adverse to the patentees was rendered Sept. 3, 1986, as to claims 1-6.
[*Official Gazette December 2, 1986.*]